(12) United States Patent
Field et al.

(10) Patent No.: US 8,584,677 B2
(45) Date of Patent: Nov. 19, 2013

(54) MEDICO-SURGICAL DEVICES

(75) Inventors: Stephen James Field, Bridge (GB); Jonathan Peter Hughes, Backford (GB); John Edward Nash, Hythe (GB)

(73) Assignee: Smiths Group PLC, London (GB)

(*) Notice: Subject to any disclaimer, the term of this patent is extended or adjusted under 35 U.S.C. 154(b) by 1082 days.

(21) Appl. No.: 12/448,723

(22) PCT Filed: Jan. 14, 2008

(86) PCT No.: PCT/GB2008/000105
§ 371 (c)(1),
(2), (4) Date: Jul. 2, 2009

(87) PCT Pub. No.: WO2008/090311
PCT Pub. Date: Jul. 31, 2008

(65) Prior Publication Data
US 2010/0089402 A1   Apr. 15, 2010

(30) Foreign Application Priority Data

Jan. 24, 2007 (GB) .................................. 0701315.4

(51) Int. Cl.
*A61M 16/00* (2006.01)
(52) U.S. Cl.
USPC ............. 128/207.14; 128/200.26; 128/207.15

(58) Field of Classification Search
USPC ............ 128/200.26, 207, 14, 207.15, 207.16
See application file for complete search history.

(56) References Cited

U.S. PATENT DOCUMENTS

| | | | |
|---|---|---|---|
| 4,767,400 A * | 8/1988 | Miller et al. ....................... 604/8 |
| 5,053,023 A * | 10/1991 | Martin .......................... 604/523 |
| 5,096,454 A | 3/1992 | Samples |
| 5,322,062 A | 6/1994 | Servas |
| 5,711,296 A | 1/1998 | Kolobow |
| 5,762,638 A * | 6/1998 | Shikani et al. ................. 604/265 |
| 6,543,451 B1 * | 4/2003 | Crump et al. ............. 128/207.14 |
| 6,694,979 B2 | 2/2004 | Deem et al. |
| 7,334,580 B2 * | 2/2008 | Smaldone et al. ........ 128/207.14 |
| 8,261,747 B2 * | 9/2012 | Smaldone et al. ........ 128/207.14 |
| 2002/0091352 A1 * | 7/2002 | McGuckin et al. ............. 604/29 |

FOREIGN PATENT DOCUMENTS

| | | |
|---|---|---|
| JP | 2004-504867 | 2/2004 |
| WO | 2005/011784 | 2/2005 |

\* cited by examiner

*Primary Examiner* — Glenn Richman
(74) *Attorney, Agent, or Firm* — Louis Woo

(57) ABSTRACT

A tracheal tube (40) or laryngeal mask has a sealing cuff (41, 2) with a surface covered by a brush-like material (44, 24) provided by closely-packed fibers (25) between 1 mm and 5 mm in length. The brush-like surface (44, 24) may be provided by coating the surface with an adhesive and using an electrostatic charge to draw fibers (25) to adhere to the adhesive.

8 Claims, 1 Drawing Sheet

MEDICO-SURGICAL DEVICES

This invention relates to medico-surgical devices.

The invention is more particularly, but not exclusively, concerned with cuffed medical tubes such as tracheal tubes and laryngeal mask airways.

Airway devices are often provided with a sealing cuff close to their patient end, which is used to seal the outside of a tube with the trachea or pharynx so that gas is confined to flow along the bore of the tube. It is important that the seal provided by this cuff be effective and does not damage patient tissue. A poor seal can allow secretions to leak past the cuff and pass down into the lower parts of the respiratory system. It is thought that such secretions entering the lungs may give rise to ventilator-associated pneumonia. The seal provided by the cuff is also important in ensuring that there is no leakage of gas since this could reduce the effectiveness of the ventilation and lead to escape of anaesthesia gases to atmosphere. One possible cause of leakage around the cuff is the presence of longitudinal creases in the cuff material, which can provide flow paths between the cuff and patient tissue.

Many different forms of cuff have been proposed in an attempt to improve the seal or interface of a tracheal tube with the trachea. Various different shapes of cuff and surface formations have been proposed, together with modifications in cuff material, coatings or thickness in an attempt to increase the effectiveness of the seal. In laryngeal masks it can also be difficult to form an effective seal. There are also other medico-surgical devices where there is a need to enhance the interface between the device and body tissue.

It is an object of the present invention to provide an alternative medico-surgical device.

According to one aspect of the present invention there is provided a medico-surgical device, characterised in that the device has a surface over a part at least of the device provided by a brush-like material.

The device may include a sealing cuff, the surface of a brush-like material being over a part at least of the cuff. The may be an airway device such as a tracheal tube or laryngeal mask. The brush-like material is preferably formed by closely packed fibers with a length between approximately 1 mm and 5 mm. The surface of brush-like material may be provided by coating the surface with an adhesive and causing to adhere to the adhesive-coated surface. An electrostatic charge may be applied to draw the to the adhesive-coated surface.

According to another aspect of the present invention there is provided an airway device including an airway tube and a sealing cuff towards one end of the tube, characterised in that the sealing cuff at least has a sealing surface of a brush-like material.

A laryngeal mask and endotracheal tube both according to the present invention will now be described, by way of example, with reference to the accompanying drawing, in which.

Figure 1:
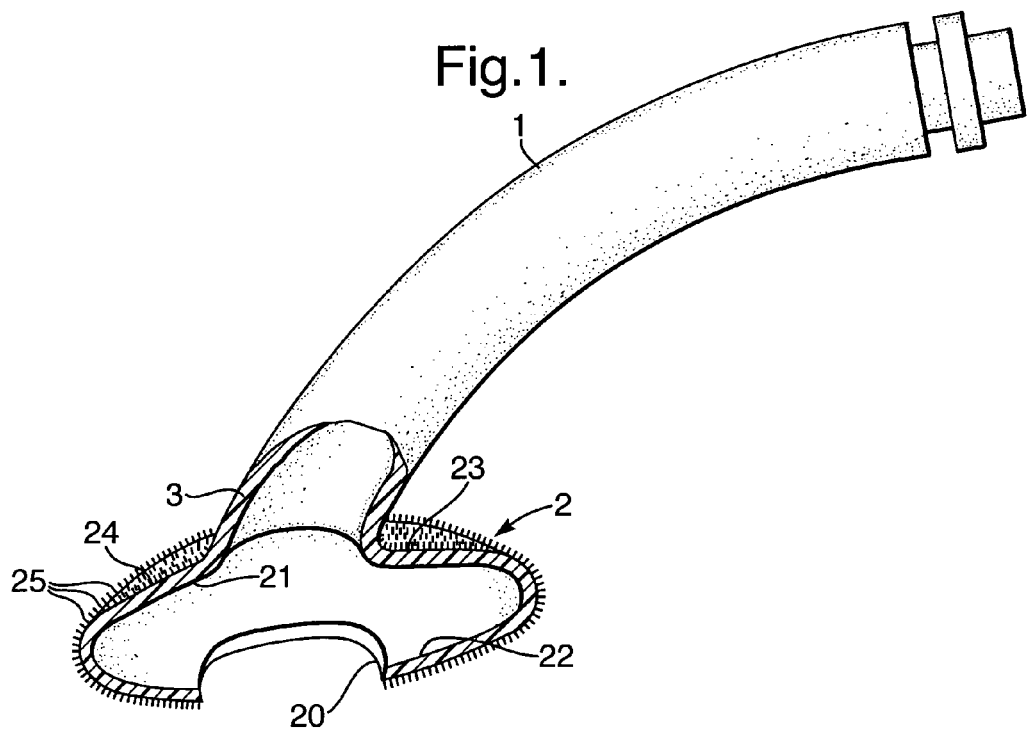
FIG. 1 is a partly cross-sectional side elevation view of the mask.

With reference first to FIG. 1, the laryngeal mask comprises an airway tube 1 and a sealing mask or cuff 2 mounted at the patient end 3 of the tube.

The airway tube 1 is of a conventional kind, being extruded or moulded of a plastics material and being curved along its length. The tube 1 is preferably flexible but is stiff enough to enable correct insertion and placement. Alternatively, the tube may have a thin wall and be highly flexible and could be reinforced by means of a helical wire or the like, in which case an introducer inserted along the bore of the tube could be used to provide additional stiffness for introduction.

The sealing cuff 2 is a separate component attached to the end of the tube 1 but could be formed integrally with the tube. The sealing cuff 2 is shaped to conform to the anatomy in the region of the pharynx and has generally hollow, oval shape. The interior of the cuff 2 opens through an aperture 20 to provide communication between the upper end of the trachea and the inside of the cuff, and hence the patient end 3 of the airway tube 1. The wall 21 of the cuff is of a plastics material and is sufficiently rigid to retain its shape but can bend to conform to larger anatomical surfaces in the pharyngeal region. In this respect it differs from conventional laryngeal mask cuffs, which are inflatable and of annular shape. The inner surface 22 of the cuff 2 is smooth; the outer surface 23 is covered with a brush-like material 24. The term "brush-like material" is intended to cover materials with a velvet or mole skin texture formed by closely-packed soft, short or villi 25 extending generally outwardly of the surface 23. The depth of the brush-like material 24 is preferably between about 1 mm and 5 mm. This brush surface 24 to the cuff 2 is more conformable than the underlying substrate material of the wall 21 and conforms readily to the smaller formations of the anatomy. The density of the brush material 24 is sufficient, by itself, to resist the flow of liquid at low pressure but may allow some gas seepage depending on the pressure drop across the region of contact. However, the effectiveness of the seal can be improved by coating the brush-like material 24 with a gel, paste or similar thick fluid or semi-fluid substance effective to fill the spaces between the villi 25.

The brush-like material 24 may be applied to the outside 23 of the cuff 2 as a coating either before or after the cuff is attached with the airway tube 1. This may be achieved by coating the cuff 2 with an adhesive and using an electrostatic charge to draw the short 25 to the adhesive-coated surface. Alternatively, the cuff 22 may be made from stock material with a ready-formed brush surface.

The sealing cuff on the laryngeal mask could instead be of the conventional inflatable, annular kind attached to one side of an oval mount member at the patient end of an airway tube. The exposed surfaces of at least the inflatable cuff would be provided with the brush-like material, which could also extend over other parts of the patient end of the assembly.

Figure 2:
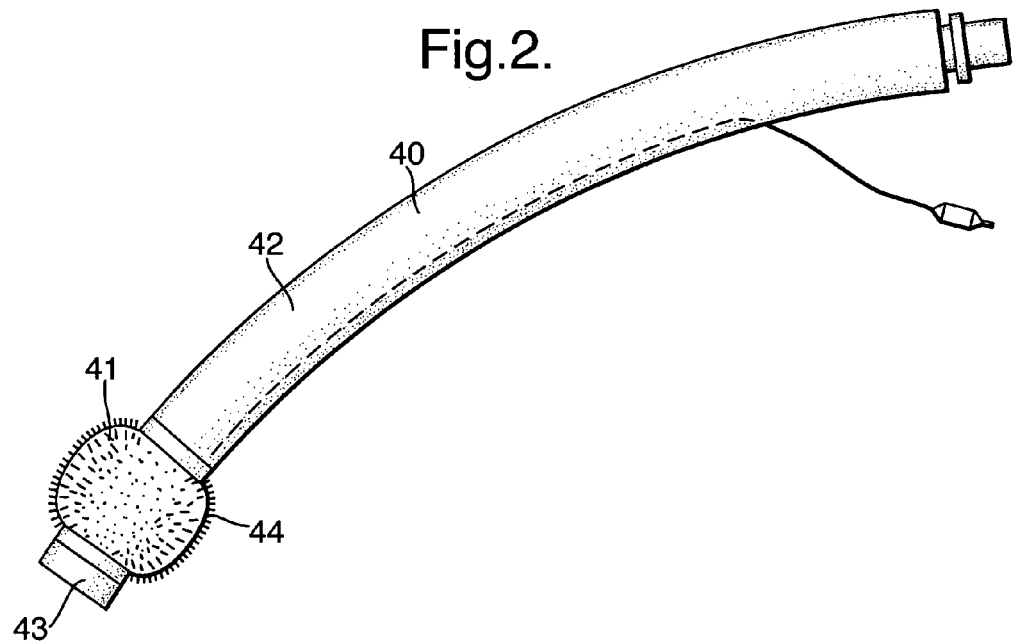
FIG. 2 is a side elevation view of a cuffed endotracheal tube

The brush-like material could also be used in a cuffed tracheal tube, such as the endotracheal tube 40 shown in FIG. 2. In this tube 40, an inflatable sealing cuff 41 encircles the tube 42 just rearwardly of its patient end 43 and the exposed surface of the cuff is covered with a brush-like material 44 of the kind described above.

The brush-like material of the present invention is not confined to use on sealing cuffs but has wider application on any surface of a medico-surgical device that is arranged to form an interface with patient tissue and where it is important that there is intimate contact.

The invention claimed is:

1. An airway device having a sealing surface over a part at least of the device arranged to form an interface with patient tissue, characterized in that the sealing surface is provided by a brush-like material formed by closely-packed fibers arranged to form an interface between the airway device with the patient tissue.

2. An airway device according to claim 1, characterized in that the device includes a sealing cuff and that the surface of the brush-like material is over a part at least of the cuff.

3. An airway device according to claim 1, characterized in that the device includes an airway tube.

4. A medico-surgical device according to claim 3, characterized in that the device is a tracheal tube.

5. A medico-surgical device according to claim 3, characterized in that the device is a laryngeal mask.

6. An airway device according to claim 1, characterized in that the closely-packed fibers have a length between approximately 1 mm and 5 mm.

7. An airway device according to claim 1, characterized in that the surface of brush-like material is provided by coating the surface with an adhesive and causing fibers to adhere to the adhesive-coated surface.

8. An airway device according to claim 7, characterized in that an electrostatic charge is applied to draw the fibers to the adhesive-coated surface.

* * * * *